(12) United States Patent
Dominiani et al.

(10) Patent No.: US 10,076,117 B2
(45) Date of Patent: Sep. 18, 2018

(54) PESTICIDE FORMULATION COMPRISING A WATER SOLUBLE ACTIVE INGREDIENT AND A PENETRATION ENHANCER AND USE OF THE SAME

(71) Applicants: ROTAM AGROCHEM INTERNATIONAL COMPANY LIMITED, Chai Wan (HK); RAINBOW TREECARE INC., Minnetonka, MN (US)

(72) Inventors: Frank Dominiani, Whitehouse Station, NJ (US); David Lawrence Anderson, Champlin, MN (US)

(73) Assignees: ROTAM AGROCHEM INTERNATIONAL COMPANY LIMITED, Chai Wan (HK); RAINBOW TREECARE INC., Minnetonka, MN (US)

( * ) Notice: Subject to any disclaimer, the term of this patent is extended or adjusted under 35 U.S.C. 154(b) by 0 days.

(21) Appl. No.: 14/471,459

(22) Filed: Aug. 28, 2014

(65) Prior Publication Data
US 2016/0057996 A1    Mar. 3, 2016

(51) Int. Cl.
*A01N 25/30*    (2006.01)
*A01N 43/90*    (2006.01)

(52) U.S. Cl.
CPC .................................. *A01N 43/90* (2013.01)

(58) Field of Classification Search
None
See application file for complete search history.

(56) References Cited

U.S. PATENT DOCUMENTS

| | | | |
|---|---|---|---|
| 6,387,388 B1 * | 5/2002 | Misselbrook | A01N 25/12 424/405 |
| 8,633,167 B2 | 1/2014 | Grossman | |
| 2011/0021353 A1 * | 1/2011 | Doolittle, Jr. | A01N 25/00 504/116.1 |
| 2013/0195946 A1 * | 8/2013 | Stamper | A01N 25/006 424/405 |

FOREIGN PATENT DOCUMENTS

CN    101263816    *    7/2010

OTHER PUBLICATIONS

CN101263816 machine translation from EPO, accessed Jan. 15, 2016.*
Proceedings 2002 U.S. Department of Agriculture Interagency Research Forum pp. 96, 98 GTR-NE-300.

* cited by examiner

*Primary Examiner* — Melissa L Fisher
(74) *Attorney, Agent, or Firm* — Dickinson Wright PLLC

(57) ABSTRACT

The present disclosure relates to an improved formulation comprising at least one water soluble active ingredient and at least one penetration enhancer. The present disclosure also relates to a use of an improved formulation comprising at least one water soluble active ingredient and at least one penetration enhancer for preventing, combating or controlling pests, particularly insect infestations, by tree injection.

11 Claims, No Drawings

PESTICIDE FORMULATION COMPRISING A WATER SOLUBLE ACTIVE INGREDIENT AND A PENETRATION ENHANCER AND USE OF THE SAME

BACKGROUND

1. Field

The present disclosure relates to an improved formulation comprising at least one water soluble active ingredient and at least one penetration enhancer. The present disclosure also relates to a use of an improved formulation comprising at least one water soluble active ingredient and at least one penetration enhancer for preventing, combating or controlling pests, particularly insect infestations, by tree injection.

2. Description of Related Art

Formulating certain water soluble active ingredients into suspension concentrate (SC) formulation is known in the art. The SC formulation is, in general, an environmentally friendly formulation, but the water soluble active ingredients in the SC formulation are often unstable and degrade easily. The active ingredients are also often easily aggregated and crystallized. Moreover, the SC formulation is not suitable for tree injection because the needle of injection device (e.g., Arborjet Tree IV™ microinfusion system (Arborjet, Inc. Woburn, Mass.)) and tree vascular system may be blocked by the aggregation of the active ingredients.

The active ingredients in an emulsified concentrate (EC) formulation are often more stable than the active ingredients in the SC formulation. However, a drawback of an injectable EC formulation is that it can be very viscous. The high viscosity of an EC formulation increases the amount of time which is required to inject the formulation into trees. The amount of time it takes to inject an EC formulation into a tree is the determinant factor in how many trees that can be treated in a fixed time period. Moreover, one of the significant costs for treating trees by injection is the labor cost. The longer the formulation takes to inject into a tree, the higher the labor cost. In addition, the high viscosity of the EC formulation makes it more likely to stick to, leave residues on, and clog injection equipment. Additional work including cleaning and frequent fixing the equipment is thus needed. The additional work further increases the labor cost and is time consuming.

Accordingly, there is a need for a stable, and residue-free formulation that provides faster uptake in trees without aggregation, for controlling pests, particularly for controlling insect infestation.

We have surprisingly found that the SL formulation of the present disclosure is extremely stable, residue-free and has a quicker uptake by tree and distribution throughout the plant and/or plant parts than other formulations, without aggregation.

SUMMARY

The present disclosure relates to an embodiment of an improved formulation comprising at least one water soluble active ingredient and at least one penetration enhancer.

The present disclosure also relates to a use of an improved formulation comprising at least one water soluble active ingredient and at least one penetration enhancer for preventing, combating or controlling pests, particularly insect infestations, by tree injection.

The present disclosure also relates to a method for increasing uptake by plants, more particularly by trees, when administered by injection, of a composition for preventing, combating or controlling pests, particularly insect infestations, by incorporating into the composition at least one penetration enhancer.

DETAILED DESCRIPTION OF SPECIFIC EMBODIMENTS

As used herein, the term "about," when used in connection with a numerical amount or range, means somewhat more or somewhat less than the stated numerical amount or range, to a deviation of ±10% of the stated numerical amount or endpoint of the range.

"Plant," as used herein, refers to all plant and plant populations such as desired and undesired wild plants or crop plants.

"Plant parts," as used herein, refers to all parts and organs of plants, such as shoot, leaves, needles, stalks, stems, fruit bodies, fruits, seeds, roots, tubers and rhizomes. Harvested materials, and vegetative and generative propagation materials, for example, cutting, tubers, meristem tissue, rhizomes, offsets, seeds, single and multiple plant cells and any other plant tissues, are also included.

"Surrounding," as used herein, refers to the place on which the plants are growing, the place on which the plant propagation materials of the plants are sown or the place on which the plant propagation materials of the plants will be sown.

"Aggregation," as used herein, means the association or clumping of sufficient amounts of component, particularly active ingredient, to be observable macroscopically, either by observing the aggregates or clumps directly, or by observing the effects the presence of such aggregates or clumps, such as clogging of nozzles or other pieces of equipment used to produce, distribute, package, or apply the composition. The degree of aggregation of the composition is determined with naked eye after storing the composition at elevated temperature. (According to procedures in the Collaborative International Pesticides Analytical Council (CIPAC) MT 46.3)

As disclosed herein, the water-soluble active ingredients include one or more of any biologically active pesticidal agent, pesticidal active ingredient or crop protection chemical which is water soluble at the concentration in which it is employed (i.e., the water-soluble active ingredients are water soluble at the field application rate). Such water-soluble active ingredients can be fungicides; herbicides, such as plant growth regulators; and insecticides, including nematicides, anti-helmentics and miticides. Exemplary, but not limiting, water-soluble active ingredients, which may be employed in the present invention, include: the fungicides: blasticidin-S, kasugamycin and hymexanol; herbicides: acifluorfen, glyphosate and glufosinate; plant growth regulators: gibberellic acid, maleic hydrazide and dikegulac; and insecticides: acephate, emamectin and emamectin benzoate. In particular, a preferred water-soluble active ingredient is emamectin, or an agriculturally acceptable salt thereof, such as the salt formed with benzoic acid, salicyclic acid, gallic acid, benzenesulfonic acid, hydrochloric and citric acid. Preferably, the water-soluble active ingredient is emamectin benzoate. One skilled in the art will readily appreciate that these active ingredients have a good water solubility, i.e., that the active ingredients will dissolve when they mix with water at the labeled application rate. For example, the application rates of acephate on commercial labels are as high as 1.33 lb (0.60 kg) in a minimum of 3 gallons (11.4 L) of water. The solubility of acephate is 650 g in 1 L of water. Acephate is fully soluble in water at the labeled application rate. The solubility of emamectin benzoate is 100 ppm in water. Thus, a typical use rate of emamectin benzoate (3.4 g) will be soluble in about 34 L of water.

The preferred water-soluble active ingredient of the present invention is emamectin benzoate. Avermectin B1a/B1b compounds, which have activity as agricultural insecticides, are disclosed in U.S. Pat. No. 4,310,519 (issued Jan. 12, 1982). The compound 4"deoxy-4"-epi-methylamino avermectin hydrochloride having insecticidal properties is disclosed in U.S. Pat. No. 4,874,749 (issued Oct. 17, 1989). Stable salts of 4"-deoxy-4"-epi-methylamino avermectin B1a/B1b are disclosed in U.S. Pat. No. 5,288,710 (issued Feb. 22, 1994).

In particular, U.S. Pat. No. 5,288,710 discloses the benzoate salt of 4"-deoxy-4"-epi-methylamino avermectin B1a/B1b (i.e., emamectin benzoate) which has the structure, e.g.:

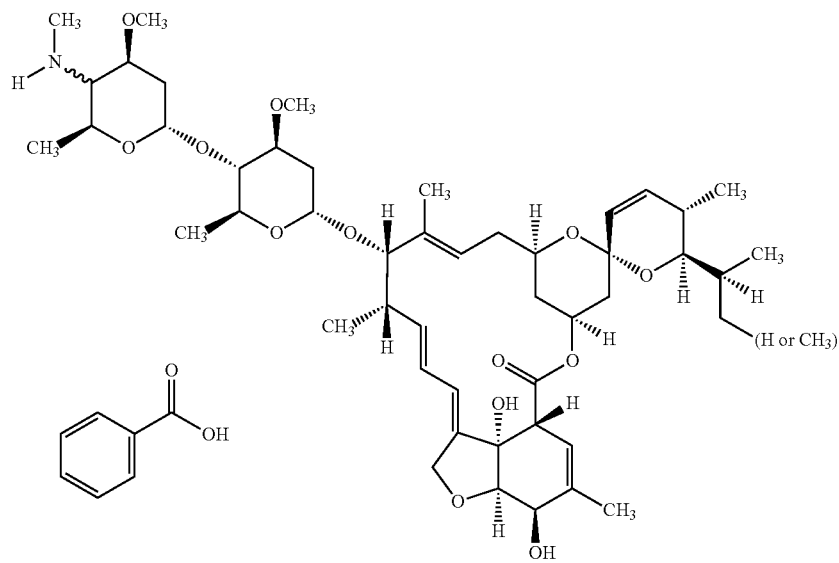

The water-soluble active ingredient is present in an amount of from about 0.1% to about 20% by weight of the formulation, preferably about 4% by weight of the formulation. Particularly, emamectin benzoate is present in an amount of from about 0.1% to about 20% by weight of the formulation, preferably about 4% by weight of the formulation.

The SL formulation of the present disclosure is extremely stable, without aggregation, and is residue-free. The SL formulation takes advantage of the properties of an organic solvent. For example, ketones (such as acetone and cyclohexanone), alcohols (such as methanol, ethanol, n-propanol, isopropanol, n-butanol, isobutanol, amyl alcohol, methyl amyl alcohol, cyclohexanol, 2-ethylhexanol, furfuryl alcohol, tetrahydrofurfuryl alcohol and d-limonene), glycol esters (such as monoethylene glycol, diethylene glycol, propylene glycol or the methyl, ethyl, n-propyl, n-butyl or t-butyl ethers thereof) and amides (such as alkanolamides, ethoxylated alkanolamides, ethylene bisamides). The solvent is preferably alcohols, more preferably tetrahydrofurfuryl alcohol. The solvent is present in an amount of from about 10% to about 90% by weight of the formulation.

Penetration enhancers used in embodiments of the composition disclosed herein may, in certain circumstances, be known in the art as "wetting agents". Surprisingly, the penetration enhancer used in embodiments of the formulation disclosed herein not only provide wetting properties to the formulation, but also facilitate the uptake by the plant and/or plant parts, particularly trees, of the active ingredient in the composition, when administered by injection into the plant.

The penetration enhancer used in embodiments of the composition disclosed herein can be selected from certain non-ionic surfactants, certain anionic surfactants and mixtures thereof.

The non-ionic surfactant can be one or more surfactants selected from alcohol oxyalkylates, alkyl phenol oxyalkylates, nonionic esters such as sorbitan esters and alkoxylates of sorbitan esters. Examples of suitable non-ionic surfactants include but are not limited to, castor oil alkoxylates, fatty acid alkoxylates, lauryl alcohol alkoxylates, nonylphenol alkoxylates, octylphenol alkoxylates, tridecyl alcohol alkoxylates, such as POE-10 nonylphenol ethoxylate, POE-100 nonylphenol ethoxylate, POE-12 nonylphenol ethoxylate, POE-12 octylphenol ethoxylate, POE-12 tridecyl alcohol ethoxylate, POE-14 nonylphenol ethoxylate, POE-15 nonylphenol ethoxylate, POE-18 tridecyl alcohol ethoxylate, POE-20 nonylphenol ethoxylate, POE-20 oleyl alcohol ethoxylate, POE-20 stearic acid ethoxylate, POE-3 tridecyl alcohol ethoxylate, POE-30 nonylphenol ethoxylate, POE-30 octylphenol ethoxylate, POE-34 nonylphenol ethoxylate, POE-4 nonylphenol ethoxylate, POE-40 castor oil ethoxylate, POE-40 nonylphenol ethoxylate, POE-40 octylphenol ethoxylate, POE-50 nonylphenol ethoxylate, POE-50 tridecyl alcohol ethoxylate, POE-6 nonylphenol ethoxylate, POE-6 tridecyl alcohol ethoxylate, POE-8 nonylphenol ethoxylate, POE-9 octylphenol ethoxylate, mannide monooleate, sorbitan isostearate, sorbitan laurate, sorbitan monoisostearate, sorbitan monolaurate, sorbitan monooleate, sorbitan monopalmitate, sorbitan monostearate, sorbitan oleate, sorbitan palmitate, sorbitan sesquioleate, sorbitan stearate, sorbitan trioleate, sorbitan tristearate, POE-20 sorbitan monoisostearate ethoxylate, POE-20 sorbitan monolaurate ethoxylate, POE-20 sorbitan monooleate ethoxylate, POE-20 sorbitan monopalmitate ethoxylate, POE-20 sorbitan monostearate ethoxylate, POE-20 sorbitan trioleate ethoxylate, POE-20 sorbitan tristearate ethoxylate, POE-30 sorbitan tetraoleate ethoxylate, POE-40 sorbitan tetraoleate ethoxylate, POE-6 sorbitan hexastearate ethoxylate, POE-6 sorbitan monstearate ethoxylate, POE-6 sorbitan tetraoleate ethoxylate, and/or POE-60 sorbitan tetrastearate ethoxylate.

Preferred nonionic surfactants include alcohol oxyalkyalates, such as POE-23 lauryl alcohol and alkyl phenol ethoxylates, such as POE (20) nonyl phenyl ether. In some embodiments, the penetration enhancer is POE-20 sorbitan monostearate ethoxylate.

The anionic surfactant can be one or more surfactants selected from sodium N-methyl-N-oleyl taurate, sodium N-methyl-N-palmityl taurate, sodium N-methyl-N-oleoyl taurate, sodium dioctyl sulfosuccinate and other sodium alkyl sulfosuccinates, sodium lauryl sulfate, alpha-(p-nonylphenyl)-omega-hydroxy poly(oxyethylene) with an average of 8-12 moles of ethylene oxide and alpha-(p-octylphenyl)-omega-hydroxy poly(oxyethylene) with an average of 7-12 moles of ethylene oxide, sodium dodecyl sulfate, sodium methylenedinaphthalene disulphonate, dibutyl naphthalene sulfonate In some embodiments, the penetration enhancer is sodium-N-methyl-N-oleyl taurate.

The penetration enhancer is generally present in an amount of from about 0.01% to about 7%, preferably from about 1% to about 5% by weight of the formulation.

"Water-soluble filler" as used herein includes any water-soluble material which may be employed to dilute the active ingredient or adjust the concentration of active ingredient in the formulation. These materials may be solids that are soluble in water, or liquids that are miscible with water, including water itself. A preferred group of water-soluble fillers are those that can be derived or obtained biologically. Appropriate water-soluble fillers include water, lactose, glucose, fructose, mannose, mannitol, sucrose, such as confectioner's sugar, black sugar, brown sugar, soft brown sugar, other sugars or saccharides, microcrystalline cellulose, powdered cellulose, calcium phosphate(s), inorganic water-soluble salts, and the like, and mixtures thereof. Examples of lactose includes hydrated α-lactose, anhydrous α-lactose, hydrated β-lactose, anhydrous β-lactose, and the like, and mixtures thereof. In some embodiment, the water-soluble filler is water. The water-soluble filler is present in an amount of from about 10% to about 30% by weight of the formulation.

"Dye" can be inorganic pigments (for example iron oxide, titanium oxide and Prussian Blue), organic dyestuffs (such as FD&C Blue No. 1, alizarin dyestuffs, azo dyestuffs and metal phthalocyanine dyestuffs), and trace nutrients (such as salts of iron, manganese, boron, copper, cobalt, molybdenum and zinc). In some embodiments, where a dye is used, a preferred dye is FD&C Blue No. 1. The dye is present in an amount of from about 0% to about 0.05%, preferably about 0.02% by weight of the formulation.

In some embodiments, conventional emulsifier, thickener, antioxidant need not be included in the SL formulation, and each or all of these components can be excluded from the composition, or included only in amounts that would constitute impurities in the composition, e.g., below 0.005 wt % of the composition, more particularly, below 0.001 wt % of the composition.

In some embodiments, an improved formulation contains:
(i) at least one water soluble active ingredient;
(ii) an organic solvent;
(iii) at least one penetration enhancer; and
(iv) water soluble filler.

In certain embodiments, an improved formulation consists of:
(i) at least one water soluble active ingredient;
(ii) an organic solvent;
(iii) at least one penetration enhancer;
(iv) water soluble filler; and
(v) dye.

In some embodiments, an improved formulation contains:
(i) emamectin benzoate, as the at least one water soluble active ingredient;
(ii) tetrahydrofurfuryl alcohol, as the organic solvent;
(iii) at least one penetration enhancer; and
(iv) water soluble filler.

In certain embodiments, an improved formulation consists of:
(i) emamectin benzoate;
(ii) tetrahydrofurfuryl alcohol;
(iii) at least one penetration enhancer;
(iv) water soluble filler; and
(v) dye.

In some embodiments, an improved formulation contains:
(i) from about 0.1% to about 20% of emamectin benzoate;
(ii) from about 10% to about 90% of tetrahydrofurfuryl alcohol;
(iii) from about 0.01% to about 7%, more particularly, from about 1% to about 5%, of a penetration enhancer, which may desirably be selected from POE-20 sorbitan monostearate ethoxylate or sodium-N-methyl-N-oleyl taurate; and
(iv) from about 10% to 30% of water soluble filler, preferably water, by weight of the formulation.

In certain embodiments, an improved formulation contains:
(i) about 4% of emamectin benzoate;
(ii) about 75% of tetrahydrofurfuryl alcohol;
(iii) about 1% of a penetration enhancer, preferably POE-20 sorbitan monostearate ethoxylate or sodium-N-methyl-N-oleyl taurate;
(iv) about 19.98% of water; and
(v) about 0.02% of dye by weight of the formulation.

It will be appreciated by one skilled in the art that the sum of the proportions of emamectin benzoate, tetrahydrofurfuryl alcohol, penetration enhancer, water and/or dye are not greater than 100% by weight of the formulation. The exact concentrations of emamectin benzoate, tetrahydrofurfuryl alcohol, penetration enhancer, water and/or dye may also vary depending on the presence of impurities.

In addition, the compositions described above may be open-ended (i.e., the term "contains" may be interpreted to mean "comprising," or closed (i.e., the term "contains" may be interpreted to mean "consisting of," or partially open and partially closed (i.e., the term "contains" may be interpreted to mean "consisting essentially of," where any additional component that affects pesticidal efficacy of the composition, or that affects the uptake of the water soluble active ingredient by the plant to which the compositions is administered affects the basic and novel characteristics of the composition).

The SL formulation of the present disclosure is extremely stable, without aggregation, has low viscosity, and is residue-free. The SL formulation of the present disclosure is therefore especially suitable for application by injection into a plant by using an injection device (e.g., Rainbow Treecare Q-Connect microinfusion system (Rainbow Treecare, Inc. Minnetonka, Minn.) or Arborjet Tree IV™ microinfusion system (Arborjet, Inc. Woburn, Mass.)) because the needle of the device and tree vascular system will not be blocked by the aggregation of the active ingredients and is less likely to stick to and leave residues on application equipment.

Furthermore, the SL formulation of the present disclosure has a quicker uptake in trees through the tree's inner capillary/vascular system during and after tree injection and distribution throughout the plant and/or plant parts than other formulations. Therefore, the SL formulation can achieve a higher efficacy.

The SL formulation of the present disclosure is useful against pests of stored grains such as *Tribolium* sp., *Tenebrio* sp., and of agricultural plants such as spider mites (*Tetranychus* sp.), aphids (*Acyrthiosiphon* sp.); migratory orthopterans such as locusts and immature stages of insects living on plant tissue. The formulation can act as a nematocide for controlling soil nematodes and plant parasites, such as *Meloidogyne* sp., which may be of importance in agriculture. Further, the formulation is active against other plant pests such as the southern army worm and Mexican bean beetle larvae.

The formulations in the present disclosure are also useful against insect pests by injecting into the plants and/or plant parts, such as pine coneworm (*Dioryctria* spp.), pine cone seed bug (suppression of *Leptoglossus* and *Tetyra* spp. in the year of treatment), aphid, bagworm, fall webworm, Japanese beetle, gypsy moth, *mimosa* webworm, oak, tussock moth, leafminers (such as *Lepidoptera*, coleoptera, pine needle scale, red palm mite, sawfly (such as elm, pine), tent caterpillars (such as Eastern, Forest, Pacific, and Western), western spruce, budworm, winter moth, flatheaded borers (such as adult and larvae of bronze birch borer, emerald ash borer and two-lined chestnut borer), clearwing borers (such as ash and *sequoia* pine pitch tube moth), *ambrosia* beetles, roundheaded borers (including asian longhorn beetles), scolytids (bark beetles) lps engraver beetles, mountain pine beetle, southern pine beetle, spruce beetle, western pine beetle, cynipid gall wasps including black oak gall, pinewood nematode, lilac borer, ash borer (*Podosesia syringae*) and so on.

Embodiments of the present invention will now be described by way of the following examples for illustrative purposes only.

EXAMPLE

Example 1—Preparation of a SL Formulation

A homogeneous liquid was obtained by mixing the liquid components in Table 1 under stirring at room temperature. The remaining components were dissolved in the liquid.

TABLE 1

| Content | Weight % | Function |
|---|---|---|
| Emamectin benzoate, 95% | 4.21 | Active ingredient |
| Sorbital monooleate ethoxylate (Toximul ®SEE-341) | 1.00 | Penetration enhancer |
| FD&C Blue No. 1 | 0.02 | Dye |
| Tetrahydrofurfuryl alcohol | 75.00 | Solvent |
| Deionized Water (q.s.) | 19.77 | Filler |

Example 2—Preparation of a SL Formulation

A homogeneous liquid was obtained by mixing the liquid components in Table 2 under stirring at room temperature. The remaining components were then dissolved in the liquid.

TABLE 2

| Content | Weight % | Function |
|---|---|---|
| Emamectin benzoate, 95% | 4.21 | Active ingredient |
| Sodium N-methyl-N-oleyl taurate | 1.00 | Penetration enhancer |
| FD&C Blue No. 1 | 0.02 | Dye |
| Tetrahydrofurfuryl alcohol | 75.00 | Solvent |
| Deionized Water (q.s.) | 19.77 | Filler |

Example 3—Preparation of an EC Formulation

A homogeneous liquid was obtained by mixing liquid components in Table 3 under stirring at room temperature. The remaining components were then dissolved in the liquid.

TABLE 3

| Content | Weight % | Function |
|---|---|---|
| Emamectin benzoate, 95% | 4.21 | Active ingredient |
| Butylated hydroxytoluene (BHT) | 1.00 | Antioxidant |
| Paraffinic oil | 6.40 | Liquid carrier |
| POE 30 castor oil | 9.00 | Liquid carrier |
| Tristyrylphenol 54M ethoxylate (EMULSOGEN ®TS54) | 9.00 | Emulsifier |
| VP/VA copolymer (LUVITEC ®VA 64 from BASF) | 18.00 | Dispersant |
| 1-Hexanol | 52.39 | Solvent |

Example 4—Preparation of a SC Formulation

A homogeneous liquid was obtained by mixing liquid components in Table 4 under stirring at room temperature. The remaining components were then dissolved in the liquid.

TABLE 4

| Content | Weight % | Function |
|---|---|---|
| Emamectin benzoate, 95% | 4.21 | Active ingredient |
| Tristyrylphenol 54M ethoxylate (EMULSOGEN ®TS54) | 9.00 | Emulsifier |
| VP/VA copolymer (LUVITEC ®VA 64 from BASF) | 2.00 | Emulsifier |
| Fatty alcohol polyglycolether GENAPOL ®T 250 | 9.00 | Surfactant |
| Sodium alkyl naphthalene sulfonate | 18.00 | Surfactant |
| Alkylpolyvinylpyrrolidone | 2.00 | Thickening agent |
| Butylated hydroxytoluene (BHT) | 1.00 | Antioxidant |
| Water | 59.00 | Filler |

Examples 5-12—Preparation of SL Formulations

Examples 5-12 were prepared by mixing the liquid components in Table 5 to obtain a homogeneous liquid and then dissolving the remaining components in the liquid.

TABLE 5

| Content | Example 1 | Example 5 | Example 6 | Example 7 | Example 8 | Example 9 | Example 10 | Example 11 | Example 12 |
|---|---|---|---|---|---|---|---|---|---|
| Emamectin benzoate, 95% (%) | 4.21 | 4.21 | 4.21 | 4.21 | 4.21 | 4.21 | 4.21 | 4.21 | 4.21 |
| Sorbital monooleate ethoxylate (Toximul ®SEE-341) (%) | 1.00 | 0 | 0.01 | 1.05 | 2.00 | 4.00 | 5.00 | 6.00 | 7.00 |
| FD&C Blue No. 1 (%) | 0.02 | 0.02 | 0.02 | 0.02 | 0.02 | 0.02 | 0.02 | 0.02 | 0.02 |
| Tetrahydrofurfuryl alcohol (%) | 75.00 | 75.00 | 75.00 | 75.00 | 75.00 | 75.00 | 75.00 | 75.00 | 75.00 |
| Deionized Water (q.s.) (%) | 19.77 | 20.77 | 20.76 | 19.72 | 18.77 | 16.77 | 15.77 | 14.77 | 13.77 |

Example 13—Comparison of the Stability of SL, EC and SC Formulations

Samples prepared in Examples 1, 3 and 4 were stored at 54° C. for 1 month, 3 months and 6 months. The procedures are followed according to CIPAC MT 46.3. The concentration of emamectin benzoate was tested at the end of each storage time by HPLC. The aggregation was measured by observation. The original concentration of emamectin benzoate in each formulation was 4%. The results are listed in Table 6.

TABLE 6

| Sample | 1 month Concentration of emamectin benzoate (%) | 1 month Aggregation | 3 month Concentration of emamectin benzoate (%) | 3 month Aggregation | 6 month Concentration of emamectin benzoate (%) | 6 month Aggregation |
|---|---|---|---|---|---|---|
| Example 1 | 4.00 | – | 4.00 | – | 4.00 | – |
| Example 3 | 3.00 | +++ | 2.50 | ++++ | 2.00 | +++++ |
| Example 4 | 3.90 | – | 3.90 | + | 3.90 | + |

Remark: "+" means small amount of aggregation. "+++++" means a lot of aggregation. "–" means no aggregation.

Example 14—Comparison of Commercial Product with the SL Formulation

Three groups of five green ash trees, *Fraxinus pennsylvanica*, 17 to 22 (Group 1), 19.5 to 23 (Group 2) and 15 to 21.5 (Group 3) inches in diameter at breast height (DBH) growing in a right of way of a residential street in St. Louis Park, Minn. were selected in Jun. 12, 2013, Sep. 12, 2013 and Sep. 26, 2013. Each treatment was injected into the root flares on opposite sides of the same tree using the Arborjet Tree IV™ microinfusion system (Arborjet, Inc. Woburn, Mass.) with 4 injection ports per side of tree. The treatments included TREE-age 4% emamectin benzoate MEC (Arborjet, Inc. Woburn, Mass.) and emamectin benzoate 4% SL prepared in the example 1. Each tree was drilled with a ⅜ inch high helix drill bit and a #4 Arborplug (Arborjet, Inc. Woburn, Mass.) was inserted. Each Tree IV™ unit was filled with 150 mL of either TREE-age emamectin benzoate MEC or 4% emamectin benzoate SL prepared in Example 1 and injected into the tree. Application times were recorded from the time the injection of chemical began until no chemical was visible within the injection system, and are shown in Table 7 below.

TABLE 7

| Group | Sample | Application time |
|---|---|---|
| Group 1 | TREE-age 4% Emamectin benzoate MEC | 14 minutes 31 seconds |
| | 4% Emamectin benzoate SL prepared in Example 1 | 10 minutes 19 seconds |
| Group 2 | TREE-age 4% Emamectin benzoate MEC | 12 minutes 6 seconds |
| | 4% Emamectin benzoate SL prepared in Example 1 | 1 minutes 20 seconds |

TABLE 7-continued

| Group | Sample | Application time |
|---|---|---|
| Group 3 | TREE-age 4% Emamectin benzoate MEC | 17 minutes 19 seconds |
| | 4% Emamectin benzoate SL prepared in Example 1 | 7 minutes 16 seconds |

TREE-age took 40.6% longer to inject than the 4% emamectin benzoate SL in Group 1, 9 times longer in Group 2 and 2.4 times longer in Group 3. The SL formulation disclosed herein has a surprisingly faster uptake than the commercially available injectable emamectin benzoate formulation. The disclosed SL formulation is therefore surprisingly more suitable for administration by injection into trees than is the commercially available formulation for tree injection, and therefore surprisingly reduces the cost of labor to treat trees in this manner.

Example 15—Comparison of Commercial Product with the SL Formulation

Three blue spruce trees, *Picea pungens*, 13 to 17 inches in diameter at breast height (DBH), three Red Oak trees, *Quercus rubra*, 8.5 to 9 inches in diameter at breast height (DBH), and three Scots Pine trees, *Pinus sylvestris*, 10.5 to 18 inches in diameter at breast height (DBH) all growing in a park in St. Louis Park, Minn. were selected on Aug. 18, 2014. Each treatment was injected into the root flares of the tree using the Q-Connect microinfusion system (Rainbow Treecare, Inc. Minnetonka, Minn.). The Q-connect utilizes 1 injection site for every 2 inches of tree diameter. The total dose for each tree was calculated and ½ of the dose was made with TREE-age 4% emamectin benzoate MEC (Arborjet, Inc. Woburn, Mass.) and the other half made with emamectin benzoate 4% SL prepared in the example 1. The treatments were alternated between injection sites around the tree to eliminate the possibility of one side of a tree uptaking product more rapidly than the other. Each injection site was drilled with a $^{15}/_{64}$th inch high helix drill bit. Each Q-Connect unit was filled with either TREE-age emamectin benzoate MEC or 4% emamectin benzoate SL prepared in Example 1 and injected into the tree. Application times were recorded from the time the injection of chemical began until no chemical was visible within the injection system, and are shown in Table 8 below.

TABLE 8

| Tree species | Average Injection time: TREE-age 4% Emamectin benzoate MEC | Average Injection Time: 4% Emamectin benzoate SL prepared in the Example 1 | Average percent time longer to inject commercial product than Example 1 formulation |
|---|---|---|---|
| blue spruce, *Picea pungens* | 22 minutes 24 seconds | 18 minutes 45 seconds | 13.5% |
| Red Oak, *Quercus rubra* | 3 minutes 42 seconds | 2 minutes 21 seconds | 57.4% |
| Scots Pine, *Pinus sylvestris* | 21 minutes 39 seconds | 16 minutes 3 seconds | 34.1% |

The commercially available formulation took between 13.5% and 57.4% longer to inject than the 4% emamectin benzoate SL disclosed herein. The SL formulation disclosed herein has surprisingly faster uptake and is surprisingly more suitable and less costly to use than the commercially available injectable emamectin benzoate formulation.

Example 16—Study on Penetration Activity

Three Red Oak trees, *Quercus rubra*, 8.5 to 9 inches in diameter at breast height (DBH) growing in a park in St. Louis Park, Minn. were selected on Aug. 18, 2014. Each treatment was injected into the root flares of the tree using the Q-Connect microinfusion system (Rainbow Treecare, Inc. Minnetonka, Minn.). The Q-connect utilizes 1 injection site for every 2 inches of tree diameter.

The total dose for each tree was calculated and tabulated below. The treatments (Example 1, Examples 5-12) were alternated between injection sites around the tree to eliminate the possibility of one side of a tree uptaking product quicker than another. Each injection site was drilled with a $^{15}/_{64}^{th}$ inch high helix drill bit. Each Q-Connect unit was filled with the SL formulations from Example 1, Examples 5-12 and injected into the tree. Application times were recorded from the time the injection of chemical began until no chemical was visible within the system which shown in Table 9 below.

TABLE 9

| Diameter at Breast Height (inch) | Dose per treatment (mL) | Example 1 | Example 5 | Example 6 | Example 7 | Example 8 | Example 9 | Example 10 | Example 11 | Example 12 |
|---|---|---|---|---|---|---|---|---|---|---|
| 9 | 15 | 1 minutes 15 seconds | 5 minutes 1 seconds | 4 minutes 50 seconds | 1 minutes 1 seconds | 55 seconds | 40 seconds | 40 seconds | 1 minutes 1 seconds | 1 minutes 50 seconds |
| 8.5 | 15 | 3 minutes 41 seconds | 4 minutes 15 seconds | 4 minutes 0 seconds | 3 minutes 21 seconds | 3 minutes 1 seconds | 3 minutes 1 seconds | 2 minutes 59 seconds | 3 minutes 20 seconds | 3 minutes 25 seconds |
| 9 | 15 | 2 minutes 6 second | 4 minutes 1 seconds | 3 minutes 45 seconds | 1 minutes 50 seconds | 1 minutes 30 seconds | 1 minutes 10 seconds | 1 minutes 9 seconds | 1 minutes 49 seconds | 1 minutes 48 seconds |
| Average | | 2 minutes 21 seconds | 4 minutes 26 seconds | 4 minutes 12 seconds | 2 minutes 4 seconds | 1 minutes 49 seconds | 1 minutes 37 seconds | 1 minutes 36 seconds | 2 minutes 3 seconds | 2 minutes 21 seconds |

The invention claimed is:

1. An injectable soluble liquid formulation comprising:
   at least one water soluble active ingredient, wherein the at least one soluble active ingredient is emamectin benzoate, and the emamectin benzoate is present in amount of 4% or about 4% by weight of the formulation, wherein the term "about" means a deviation of not more than ±10% by weight,
   at least one penetration enhancer, wherein the at least one penetration enhancer is sorbital monooleate ethoxylate present in an amount from 0.01% to 7.0% by weight of the formulation to facilitate uptake by a plant of the water soluble active ingredient when administered by injection into a plant, and an organic solvent, wherein the organic solvent is tetrahydrofurfuryl alcohol, and the tetrahydrofurfuryl alcohol is present in an amount of from about 75% to about 90% by weight of the formulation.

2. The soluble liquid formulation according to claim 1, further comprising a water soluble filler.

3. The soluble liquid formulation according to claim 1, further comprising water.

4. The soluble liquid formulation according to claim 1, optionally further comprising a dye.

5. The soluble liquid formulation according to claim 4, wherein the dye is FD&C Blue No. 1.

6. The soluble liquid formulation according to claim 3, wherein the water is present in an amount of from about 10% to about 30% by weight of the formulation.

7. The soluble liquid formulation according to claim 4, wherein the dye is present in an amount of from about 0% to about 0.05%.

8. An injectable soluble liquid formulation comprising:
(i) about 4% of emamectin benzoate;
(ii) about 75% of tetrahydrofurfuryl alcohol;
(iii) about 1% of sorbital monooleate ethoxylate;
(iv) about 19.98% of water; and
(v) optionally about 0.02% of dye by weight of the formulation.

9. A method of preventing, combating or controlling insect pest infestation in plants comprising applying to the plants and/or parts thereof a soluble liquid formulation according to claim 1 by injecting the soluble liquid formulation into the plants and/or plant parts.

10. The method according to claim 9, wherein the plant is a tree.

11. The method according to claim 9, wherein the pest infestation is an infestation of one or more pests selected from the group consisting of pine coneworm (*Dioryctria* spp.), pine cone seed bug, aphid, bagworm, fall webworm, japanese beetle, gypsy moth, *mimosa* webworm, oak, tussock moth, leafminers coleoptera, pine needle scale, red palm mite, sawfly, tent caterpillars, western spruce, budworm, winter moth, flatheaded borers, clearwing borers, *ambrosia* beetles, roundheaded borers, scolytids, bark beetles, lps engraver beetles, mountain pine beetle, southern pine beetle, spruce beetle, western pine beetle, cynipid gall wasp, black oak gall wasp, pinewood nematode, lilac borer and ash borer (*Podosesia syringae*).

* * * * *